United States Patent [19]
Chevalier et al.

[11] Patent Number: 6,156,804
[45] Date of Patent: *Dec. 5, 2000

[54] USE OF A MICRODISPERSION OF WAX IN A COSMETIC OR DERMATOLOGICAL COMPOSITION

[75] Inventors: Veronique Chevalier, Villecresnes; Valerie Hurel, Gif/S/Yvette, both of France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 09/245,297

[22] Filed: Feb. 5, 1999

[30] Foreign Application Priority Data

Feb. 9, 1998 [FR] France .................. 98 01494

[51] Int. Cl.⁷ .................................................. A61K 47/00
[52] U.S. Cl. ............................................... 514/787
[58] Field of Search ............................... 424/59, 60, 63, 424/64; 514/938, 847, 787

[56] References Cited

U.S. PATENT DOCUMENTS 5,733,531  3/1998  Mitchnick et al. ...................... 424/59

FOREIGN PATENT DOCUMENTS

| | | |
|---|---|---|
| 0 394 078 | 10/1990 | France . |
| 0 446 094 A1 | 9/1991 | France . |
| 2 666 015 | 2/1992 | France . |
| 0 557 196 A1 | 8/1993 | France . |
| 822824 | 7/1979 | Russian Federation ......... A61K 7/00 |
| 1738081 | 2/1992 | Russian Federation ......... A61K 7/00 |
| 822824 | 4/1981 | U.S.S.R. ......................... A61K 7/00 |
| 1738081 | 5/1992 | U.S.S.R. ......................... A61K 7/00 |

OTHER PUBLICATIONS

Database WPI, Section CH, Week 8715, Derwent Publications Ltd., London, GB; Class A96, AN 87–106529.

Data Base WPI, Section CH, Week 8815, Derwent Publications Ltd., London, GB, Class D21, AN 88–103905.

*Primary Examiner*—William R. A. Jarvis
*Assistant Examiner*—Vickie Kim
*Attorney, Agent, or Firm*—Oblon, Spivak, McClelland, Maier & Neustadt, P.C.

[57] ABSTRACT

Wrinkles and fine lines of the skin are treated and/or cutaneous and/or subcutaneous slackening of the skin is combated and/or the radiance of the skin is revived by topically treating the skin with a microdispersion of wax in a topical composition.

21 Claims, No Drawings

USE OF A MICRODISPERSION OF WAX IN A COSMETIC OR DERMATOLOGICAL COMPOSITION

BACKGROUND OF THE INVENTION

1. Field of the Invention

The present invention relates to the use of a microdispersion of wax in the preparation of a cosmetic composition, or in the preparation of a dermatological composition, for topical application as an active agent which is intended to prevent and/or treat certain signs of endogenous and/or exogenous ageing.

2. Description of the Background

Ageing of the skin results from the effects of intrinsic and extrinsic factors on the skin. Clinically, the signs of ageing are reflected by the appearance of wrinkles and fine lines, by slackening of the cutaneous and subcutaneous tissues, by loss of skin elasticity, by atonia of the skin texture and by yellowing of the skin, which becomes duller and loses its radiance. On the areas of skin which have been exposed to sunlight throughout life—essentially the face, the neckline, the hands and the forearms—pigmentation marks, telangiectasias and elastosis are often observed.

Some of these signs are more particularly associated with intrinsic or physiological ageing, i.e. with age-related ageing, whereas others are more specific for extrinsic ageing, i.e. ageing caused in general by the environment; this more particularly concerns light-induced ageing which results from exposure to sunlight, to light or to any other radiation.

The changes in the skin resulting from intrinsic or physiological ageing are the consequence of a genetically programmed senescence involving endogenous factors. This intrinsic ageing gives rise especially to a slowing-down of renewal of the skin cells. Histologically, the skin is thinner overall, both at the epidermal and dermal levels. The density of the fibrous macromolecules in the dermis (elastin and collagen) is reduced. In contrast, extrinsic ageing entails histopathological changes such as an excessive accumulation of elastic material in the upper dermis and degeneration of the collagen fibers.

The composition of the present invention is formulated to treat wrinkles and fine lines in the skin, the slackening of the cutaneous and subcutaneous tissues of the skin and the radiance of the skin. Slackening of the cutaneous and subcutaneous tissues is reflected by an atonic skin texture, slackening of the skin's microrelief, reduced skin firmness and an overall flaccid skin.

Many compositions are known which claim to treat the wrinkles and fine lines in the skin or to firm up skin tissues, but these compositions only provide incomplete and temporary treatment of these morphological disorders. Thus, a need continues to exist for a composition for topical application which can treat wrinkles and fine lines more effectively and firm up skin tissues.

SUMMARY OF THE INVENTION

Accordingly, one object of the present invention is to provide a skin treatment composition which gives aged skin a radiance comparable to that of younger skin.

Another object of the invention is to provide a microdispersion of wax in a cosmetic composition or in a dermatological composition, as an active agent which is intended to prevent and/or treat the appearance of wrinkles and fine lines, to combat cutaneous and/or subcutaneous slackening and to revive the radiance of the skin.

Still a further object of the invention is to provide a microdispersion of wax in a cosmetic composition, or in a dermatological composition, as an active agent which is intended to prevent and/or treat the loss of skin elasticity, and/or atonia of the texture of the skin and/or slackening and/or flabbiness (or collapse) of the skin's microrelief, cutaneous and/or subcutaneous flaccidity, and/or as an active agent which is intended to firm up the skin and/or to tone up the texture of the skin.

Yet another object of the invention is to provide a process for the cosmetic treatment of wrinkles and/or fine lines in the skin and/or for cutaneous and/or subcutaneous slackening of the skin by firming up the skin and/or to revive the radiance of the skin, this process comprising the application to the skin of a cosmetic composition containing at least one microdispersion of wax.

Briefly, these objects and other objects of the present invention as hereinafter will become more readily apparent can be attained by a method of topically treating the skin, comprising applying to the skin a cosmetic composition of a microdispersion of wax as an active agent, thereby preventing and/or treating the signs of endogenous and/or exogenous ageing of the skin, which signs include winkles and fine lines of the skin, and/or cutaneous and/or subcutaneous slackening of the skin, and also reviving the radiance of the skin.

DETAILED DESCRIPTION OF THE PREFERRED EMBODIMENTS

U.S. Pat. No. 1,335,288 teaches the use of emulsified waxes in compositions which are intended to treat slackening of the skin. However, in the compositions described in the document, the emulsified waxes function as an emulsifier, and their use as an active agent to prevent and/or treat the appearance of the signs of ageing of the skin is neither mentioned nor suggested.

Another publication, U.S. Pat. No. 1,250,297, teaches that waxes can function as agents for the treatment of aged skin, in particular wrinkles in the skin. However, it has now been discovered that, unexpectedly, microdispersions of wax are much more effective than standard waxes in the prevention and treatment of the signs of ageing of the skin.

Microdispersions of wax, which are stable dispersions of colloidal particles of wax, are known and can be prepared according to known methods: see for example "Microemulsions Theory and Practice", L. M. Prince Ed., Academic Press (1977) pages 21–32.

The particles in the microdispersion of wax are less than 5 $\mu$m in size, preferably less than 0.5 $\mu$m in size. These particles consist essentially of a wax or of a mixture of waxes. The melting point of the wax or of the mixture of waxes preferably ranges from 50–150° C. In addition, the particles in the microdispersion can contain a small amount of oily or pasty fatty additives, one or more surfactants and one or more common liposoluble active ingredients, as will be specified below.

The composition generally contains from 0.1–40% by weight of waxes, in particular 5–30%, and a sufficient amount of at least one emulsifier. The amount of emulsifier is an amount which is sufficient to provide a microdispersion of wax as defined above. This sufficient amount can be determined in each case by routine experiments.

The waxes are natural (animal or plant) or synthetic substances which are solid at room temperature (20–5° C.). They are insoluble in water, soluble in oils and are capable of forming a water-repellent film. A definition of waxes is provided by, for example, P. D. Dorgan, Drug and Cosmetic Industry, December 1983, pp. 30–33.

The wax(es) which constitute the waxy mixture is (are) selected, in particular, from carnauba wax, candelilla wax and alfalfa wax, and mixtures thereof.

In addition to these waxes, the mixture of waxes can also contain one or more of the following waxes or family of waxes:

paraffin wax,
ozokerite,
plant waxes such as olive wax, rice wax, hydrogenated jojoba wax or the absolute waxes of flowers such as the essential wax of blackcurrant flower sold by the company Bertin (France),
animal waxes such as beeswaxes or modified beeswaxes (cerabellina);
other waxes or waxy starting materials;
marine waxes such as those sold by the company Sophim under the identifier M82;
natural or synthetic ceramides, and polyethylene or polyolefin waxes in general.

The carnauba (extract of *Copernica cerifera*), candelilla (extract of *Euphorbia cerifera* and of *Pedilantus pavonis*) and alfalfa (extract of *Stipa tenacissima*) plant waxes are commercial products.

Ceramides are the main lipids which constitute the interconeocytic spaces of the stratum corneum. They are described in particular by Downing in Science, 1982, vol. 18, P. 1261–1262. Synthetic analogues are also known such as the ceramides HO3 sold by the company Cosmind.

In the mixture of waxes, the carnauba and/or candelilla and/or alfalfa wax represents at least 20%, preferably at least 50%, by weight relative to the total weight of the mixture of waxes.

The wax or the mixture of waxes can contain, besides the waxes mentioned above, at least one other wax and/or at least one oil, it being understood that the mixture of waxes and optionally of oil has a finishing melting point of greater than 50° C.

The mixture of waxes can thus be combined with one or more fatty additives (oily or pasty). Suitable fatty additives include, but are not limited to:

plant oils such as sunflower oil, jojoba oil, and the like;
mineral oils such as liquid paraffin;
fluid silicone oils having a viscosity ranging from, in particular, 0.65–100,000 centistokes, i.e. from $0.65 \times 10^{-4}$ and $10 \text{ m}^2 \cdot \text{s}^{-1}$, preferably from 5–5000 centistokes, i.e. from $5 \times 10^{-4}$ to $5 \times 10^{-1}$ $m2 \cdot s^{-1}$;
fluoro oils;
petroleum jelly;
lanolin.

The mixture of oil(s) and/or of pasty fatty additives can represent up to 30%, preferably not more than 10%, of the weight of waxes.

It is also possible to introduce liposoluble active ingredients into the microparticulate waxy phase.

When they are present, the liposoluble active ingredient(s) represent(s) not more than 30%, preferably not more than 10%, of the weight of the microparticles.

The use of surfactants as emulsifiers in the preparation of microdispersions of waxes is known. The microdispersion can be prepared using anionic, cationic and/or nonionic surfactants, in a known manner.

The percentage of surfactant(s) in the final composition generally ranges from 0.01–25% approximately and, in particular, can range from 0.1–10%.

The wax(es)/emulsifier(s) weight ratio can range, for example, from 1–30 and in particular from 2–10.

Suitable anionic surfactants include, in particular, fatty acid salts, for example, alkaline salts or organic salts such as amine salts, the said fatty acids containing, for example, from 12–16 carbon atoms and possibly containing a double bond, as in the case of oleic acid, the alkaline salts or salts of organic bases of alkylsulfuric and alkylsulfonic acids containing 12–18 carbon atoms, alkylarylsulfonic acids in which the alkyl chain contains from 6–18 carbon atoms, the aryl group being, for example, a phenyl group. Suitable surfactants also include ether-sulfates, in particular the products of sulfation of polyalkoxylated alkylphenol fatty alcohols in which the aliphatic chain contains from 6–20 carbon atoms and the polyalkoxylated chain contains from 1–30 oxyalkylene units, in particular oxyethylene, oxypropylene or oxybutylene units.

All of these anionic surfactants are well-known and many of them are commercial products.

Suitable nonionic surfactants include mainly polyalkoxylated and/or polyglycerolated surfactants, in particular, polyalkoxylated and/or polyglycerolated fatty acids or fatty acid amides; polyalkoxylated and/or polyglycerolated fatty alcohols or alkylphenols; polyalkoxylated and/or polyglycerolated fatty acid esters of polyols, polyalkoxylated and/or polyglycerolated alkanediols or 1,2- or 1,3-alkenediols; and polyalkoxylated and/or polyglycerolated alkyl ethers of alkanediols or 1,2- or 1,3-alkenediols. For example, the optionally unsaturated fatty acids or alcohols contain 12–24 carbon atoms, the alkyl chain of the alkylphenols contains 6–16 carbon atoms, the alkanediols or alkenediols contain from 9–24 carbon atoms, the alkyl in the alkyl ethers contains from 4–20 carbon atoms, and the number of oxyalkylene units or of $(CH_2CHOHCH_2O)$ units can range from 2–40.

The polyalkoxylated nonionic derivatives include, in particular, polyoxyethylenated, optionally polyoxypropylenated, derivatives.

The polyalkoxylated fatty acids are commercial products, in particular the products sold under the brand name Myrj by the company Atlas.

The polyoxyethylenated fatty acid esters of polyols for which the polyol is sorbitol are known products (Polysorbate and products sold under the brand name Tween by the company Atlas). When the polyol is glycerol, the products sold under the brand name Brij by the company Atlas can be used.

The polyglycerolated fatty alcohols, the polyglycerolated alkanediols or alkenediols, or the polyglycerolated alkyl ethers of alkanediols or of alkenediols can be prepared, for example, according to the processes described in French patents 1,477,048, 2,025,681, 2,091,516 and 2,465,780 or according to similar processes.

The polyglycerolated fatty acids or fatty acid amides are described, in particular, in French patent 1,484,723 or else are commercial products such as those sold under the brand name Plurol (Gattefossé) or Drewpol (Stefan Company) or Decaglyn (Nikko Chemical).

Other nonionic surfactants include, for example:

triglyceryl alkylcarbamates of the formula: $R-NHCOOCH(CH_2OCH_2CHOHCH_2OH)_2$ in which R represents a saturated or unsaturated alkyl group of 10–20 carbon atoms. These compounds are described in patent EP 0,420,761;
oxyethylenated or propoxylated derivatives of lanolin alcohols, of lanolin fatty acids, or mixtures thereof.

Such surfactants are sold by the company Amerchol under the brand name Solulan.

Suitable anionic surfactants include, in particular, quaternary ammonium derivatives such as Arquad 16-50, Arquad 18-50, Arquad T-50, Arquad 2C-75, Ethoaquad c/12 and Ethoquad 0/12, sold by the company Armak Chemicals.

The use of nonionic surfactants is preferred.

It is also possible to prepare microdispersions of waxes using commercial mixtures of self-emulsifying waxes containing the wax and the surfactants.

It is possible to use, for example, the wax sold under the name Cire Auto Lustrante OFR by the company Tiscco, which contains carnauba wax and paraffin wax, combined with nonionic emulsifiers, or the self-emulsifying wax sold under the name Cerax A.O. 28/B by La Ceresine, which contains alfalfa wax combined with a nonionic emulsifier.

These commercial mixtures allow microdispersions of waxes to be prepared by addition of water according to the process described above.

It is also possible to use commercially available ready-to-use microdispersions of waxes, such as the products from the series Slip-Aid from the company Daniel Products Company, or the Aguacer products from the company Cerachemie.

The microdispersions of waxes can be diluted with water without harming the stability of the microdispersion. They can thus be in the form of concentrated compositions whose proportion of ingredients can be adjusted to a desired value by simple addition of water.

The composition contains a cosmetically or dermatologically acceptable medium, i.e. a medium which is compatible with skin tissues. Thus, the composition can be applied to the entire human body.

In a known manner, the cosmetic or dermatological composition of the invention can also contain adjuvants which are common in the cosmetics, pharmaceutical and dermnatological fields such as hydrophilic or lipophilic gelling agents, hydrophilic or lipophilic active agents, preserving agents, antioxidants, solvents, fragrances, fillers, screening agents, bactericides, odor absorbers and dyestuffs. The amounts of these various adjuvants are amounts normally used conventionally in the field considered, and, for example, range from 0.01–10% of the total weight of the composition. Depending on their nature, these adjuvants can be introduced into the fatty phase, into the aqueous phase and/or into the lipid spherules.

Suitable solvents which can be used in the invention include lower alcohols, in particular, ethanol and isopropanol, and propylene glycol.

Suitable hydrophilic gelling agents include carboxyvinyl polymers (carbomer), acrylic copolymers such as acrylate/alkylacrylate copolymers, polyacrylamides, polysaccharides such as hydroxypropylcellulose, natural gums and clays.

Suitables lipophilic gelling agents include modified clays such as bentones, metal salts of fatty acids such as aluminum stearates, and hydrophobic silica, or alternatively ethylcellulose and polyethylene.

Suitable lipophilic or hydrophilic active agents which are present in the composition to improve the treatment of wrinkles and fine lines, to combat cutaneous and/or subcutaneous slackening and/or to give radiance to the skin, include, for example, retinoids which include retinol and its esters, retinal, retinoic acid and its derivatives, retinoids, and in particular those described in documents FR 2,570,377, EP 0 199 636, EP 0 325 540 and EP 0 402 072, α-hydroxy acids such as glycolic, lactic, malic, citric, tartaric or mandelic acid), β-hydroxy acids such as salicylic acid and its derivatives, in particular its alkyl derivatives, α-keto acids, β-keto acids, peroxides such as benzoyl peroxide, vitamins, in particular vitamins E and F. anti-free-radical active agents such as superoxide dismutase, selenium, zinc, beta-carotenes, and tensioning polymers of natural or synthetic origin.

The composition can also contain natural or synthetic, oestrogenic, progestative or androgenic hormones such as progesterone, testosterone, anhydrous oestradiol, broparestrol, oestrone, pregnenolone acetate, pregnenolone, 17-β-hydroxyprogesterone, testosterone propionate, androstenedione and androstanediols.

The compositions of the invention can be prepared by hot-formation of a microemulsion. More specifically, these compositions are prepared by a process in which the wax and the emulsifier are heated to a temperature above the melting point of the wax, but not above 100° C., optionally in the presence of some of the water, until the wax has completely melted. The water, or the remainder of the water, which has been brought to a temperature at least equal to the said temperature, is gradually added with stirring, until a microemulsion of wax in a continuous aqueous phase is formed, and the mixture is then left to cool to room temperature. A stable microdispersion of wax is obtained.

The process is performed with stirring and with an amount of surfactant which is sufficient for the sizes of the wax microparticles to be less than 1000 nm, and preferably less than 500 nm.

The liposoluble ingredients, for example ceramides, are generally added to the wax before the microdispersion is made.

The water-soluble ingredients can be added to the water used to make the microdispersion, or to the microdispersion of wax finally obtained.

Similarly, the secondary ingredients, which may be present in the composition, are added, depending on the case, either into the starting materials or into the finished composition.

Having now generally described the invention, a further understanding can be obtained by reference to certain specific examples which are provided herein for purpose of illustration only and are not intended to be limiting unless otherwise specified.

The percentages of starting material are weight percentages relative to the total weight of the composition. The names of the constituents are given in terms of the INCI name.

EXAMPLES

Example 1

Anti-wrinkle Cream (Water-in-Oil Emulsion)

Phase A

| | |
|---|---|
| Hydrogenated polyisobutene | 5.5% |
| Isostearyl neopentanoate | 3.5% |
| PEG-20 stearate | 1% |
| Glyceryl stearate and PEG 100 stearate | 2% |
| Cetyl alcohol | 0.5% |
| Stearyl alcohol | 0.5% |
| Stearic acid | 3% |

Phase A'

| | |
|---|---|
| Cyclomethicone | 11% |

Phase C

| | |
|---|---|
| Polyacrylamide and C13-C14 isoparaffin and laureth-7 | 1.7% |

Phase D

| | |
|---|---|
| Polyethylene (Aquacer 513 sold by the company Cerachimie) | 20% |

Phase B

| | |
|---|---|
| Preserving agents | qs |
| Sodium hydroxide | 0.03% |
| Water | qs 100% |

Procedure

Phase A is heated with stirring until homogeneous. After cooling Phase A' is added. Phase B is heated with stirring, and B is then poured into A with continued stirring. After cooling to 50° C., Phase C is incorporated into the emulsion, followed, at 40° C., by Phase D.

Example 2

Anti-ageing Serum

| | |
|---|---|
| Polyacrylamide and C13-C14 isoparaffin and laureth-7 | 1% |
| Xanthan gum | 0.2% |
| PVM/MA decadiene crosspolymer | 0.2% |
| Triethanolamine | 0.2% |
| Polyethylene (Aguacer 513 sold by the company Cerachimie) | 10% |
| Preserving agent | qs |
| Water | qs 100% |

Procedure

Xanthan gum and the polymer (PVM/MA decadiene crosspolymer) are dispersed in hot water with stirring, with the preserving agents and the triethanolamine. The mixture is cooled to 40° C. and the microwax (polyethylene) and the polyacrylamide are incorporated in the aqueous medium, with continued stirring.

The disclosure of French priority application serial number 9801494 filed Feb. 9, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A method of topically treating the skin, comprising:
    applying to the skin, a cosmetic composition containing an active agent consisting essentially of a microdispersion of wax, which treats the signs of endogenous ageing of the skin, which treats the signs of exogenous ageing of the skin, or both.
2. The method of claim 1, wherein the particles of wax of the microdispersion of wax have a size of $\leq 5$ μm.
3. The method of claim 2, wherein the particles of wax have a size of $\leq 0.5$ μm.
4. The method of claim 1, wherein the wax or the wax as a mixture of waxes has a melting point ranging from 50–150° C.
5. The method of claim 1, wherein the wax composition contains from 0.1–40% by weight of wax.
6. A method of topically treating the skin, comprising:
    applying to the skin, a cosmetic composition containing an active agent consisting essentially of a microdispersion of wax, which treats the wrinkles and/or fine lines of the skin.
7. The method of claim 6, wherein the particles of wax of the microdispersion of wax have a size of $\leq 5$ μm.
8. The method of claim 7, wherein the particles of wax have a size of $\leq 0.5$ μm.
9. The method of claim 6, wherein the wax or the wax as a mixture of waxes has a melting point ranging from 50–150° C.
10. The method of claim 6, wherein the wax composition contains from 0.1–40% by weight of wax.
11. A method of topically treating the skin, comprising:
    applying to the skin, a cosmetic composition containing an active agent consisting essentially of a microdispersion of wax, which combats cutaneous, subcutaneous or a combination of both slackening of the skin, which combats the loss of skin elasticity, which combats atonia of the texture of the skin, which combats slackening, flabbiness or both of the skin's microrelief, which combats cutaneous, subcutaneous or both flaccidity of the skin or a combination thereof.
12. The method of claim 11, wherein the particles of wax of the microdispersion of wax have a size of $\leq 5$ μm.
13. The method of claim 12, wherein the particles of wax have a size of $\leq 0.5$ μm.
14. The method of claim 11, wherein the wax or the wax as a mixture of waxes has a melting point ranging from 50–150° C.
15. The method of claim 11, wherein the wax composition contains from 0.1–40% by weight of wax.
16. A method of topically treating the skin, comprising:
    applying to the skin, a cosmetic composition containing an active agent consisting essentially of a microdispersion of wax, which firms-up the skin, which tones-up the texture of the skin, which revives the radiance of the skin or combinations thereof.
17. The method of claim 16, wherein the particles of wax of the microdispersion of wax have a size of $\leq 5$ μm.
18. The method of claim 17, wherein the particles of wax have a size of $\leq 0.5$ μm.
19. The method of claim 16, wherein the wax or the wax as a mixture of waxes has a melting point ranging from 50–150° C.
20. The method of claim 16, wherein the wax composition contains from 0.1–40% by weight of wax.
21. A method of topically treating the skin, comprising:
    applying to the skin, a cosmetic composition containing an active agent consisting essentially of a microdispersion of wax in which the wax particles have a particle size of $\leq 5$ μm and a melting point ranging from 50 to 150° C., which treats the signs of endogenous ageing of the skin, which treats the signs of exogenous ageing of the skin, or both.

* * * * *